US011331362B2

(12) United States Patent
Su et al.

(10) Patent No.: US 11,331,362 B2
(45) Date of Patent: May 17, 2022

(54) COMPOSITION OF PLANT INGREDIENTS, HERBAL COMPOSITION AND PREPARATION METHOD OF THE HERBAL COMPOSITION

(71) Applicant: NATIONAL RESEARCH INSTITUTE OF CHINESE MEDICINE, MINISTRY OF HEALTH AND WELFARE, Taipei (TW)

(72) Inventors: Yi-Chang Su, Taipei (TW); Wen-Hui Chiou, Taipei (TW); Yao-Haur Kuo, Taipei (TW); Keng-Chang Tsai, Taipei (TW); Chia-Ching Liao, Taipei (TW); Wen-Chi Wei, Taipei (TW); Chun-Tang Chiou, Taipei (TW); Kuo-Ming Yeh, Taipei (TW); Yi-Chia Huang, Taipei (TW); Chien-Jung Lin, Taipei (TW); Jui-Shan Lin, Taipei (TW)

(73) Assignee: NATIONAL RESEARCH INSTITUTE OF CHINESE MEDICINE, MINISTRY OF HEALTH AND WELFARE, Taipei (TW)

( * ) Notice: Subject to any disclaimer, the term of this patent is extended or adjusted under 35 U.S.C. 154(b) by 0 days.

(21) Appl. No.: 17/128,234

(22) Filed: Dec. 21, 2020

(65) Prior Publication Data
US 2021/0353703 A1 Nov. 18, 2021

Related U.S. Application Data

(60) Provisional application No. 63/026,733, filed on May 19, 2020, provisional application No. 63/025,224, filed on May 15, 2020.

(51) Int. Cl.
| | | |
|---|---|---|
| *A61K 36/539* | (2006.01) | |
| *A61K 36/484* | (2006.01) | |
| *A61K 36/534* | (2006.01) | |
| *A61K 36/78* | (2006.01) | |
| *A61K 36/238* | (2006.01) | |
| *A61K 36/605* | (2006.01) | |
| *A61K 36/42* | (2006.01) | |
| *A61K 36/575* | (2006.01) | |
| *A61K 36/31* | (2006.01) | |
| *A61P 31/14* | (2006.01) | |

(52) U.S. Cl.
CPC .......... *A61K 36/539* (2013.01); *A61K 36/238* (2013.01); *A61K 36/31* (2013.01); *A61K 36/42* (2013.01); *A61K 36/484* (2013.01); *A61K 36/534* (2013.01); *A61K 36/575* (2013.01); *A61K 36/605* (2013.01); *A61K 36/78* (2013.01); *A61P 31/14* (2018.01); *A61K 2236/331* (2013.01)

(58) Field of Classification Search
CPC .. A61K 2300/00; A61K 36/238; A61K 36/31; A61K 36/42; A61K 36/484; A61K 36/534; A61K 36/539; A61K 36/575; A61K 36/605; A61K 36/78; A61K 2236/331; A61P 31/14
See application file for complete search history.

(56) References Cited

FOREIGN PATENT DOCUMENTS

CN 101099787 A 1/2008

OTHER PUBLICATIONS

Yang, Yichang "Use of herbal drugs to treat COVID-19 should be with caution" The Lancet, vol. 395, May 30, 2020 (published online May 15, 2020), pp. 1689-1690; doi: 10.1016/S0140-6736(20)31143-0. (Year: 2020).*
Wang M, et al "Influence of Honey-Roasting on the Main Pharmacological Activities and the Water-Soluble Active Glycosides of Licorice" Afr J Tradit Complement Altern Med. 2012 (pub. online Dec. 29, 2011),9(2),pp. 189-196; doi: 10.4314/ajtcam.v9i2.2. (Year: 2011).*
Zeng M, et al "Traditional Chinese medicine Lianhua Qingwen treating corona virus disease 2019(COVID-19): Meta-analysis of randomized controlled trials" PLOS One, Sep. 11, 2020, 7 pages ; doi.org/10.1371/journal.pone.0238828. (Year: 2020).*
Deng-Hai Zhang et al., In silico screening of Chinese herbal medicines with the potential to directly inhibit 2019 novel coronavirus, Journal of Integrative Medicine, Mar. 2020 (Available online Feb. 20, 2020), 18(2): 152-158.
Chen Huijun et al., Patent Big Data Exploring Chinese Medicinal Materials for Prevention and Treatment of COVID-19, China Invention & Patent, Mar. 2020, 17(3): 57-61.

(Continued)

*Primary Examiner* — Aaron J Kosar

(57) ABSTRACT

A composition of plant ingredients, a herbal composition for inhibiting coronavirus and cytokine storm, and a preparation method of the herbal composition are introduced. The composition of plant ingredients has Heartleaf Houttuynia, Indigowood Root, Fineleaf Nepeta, Saposhnikovia Root, Mulberry Leaf, Scutellaria Root, Mongolian Snakegourd Fruit, Magnolia Bark, Peppermint Herb and Baked Liquorice Root. The herbal composition has 1 to 20 parts by weight of Heartleaf Houttuynia, Indigowood Root, Fineleaf Nepeta, Saposhnikovia Root, Mulberry Leaf, Scutellaria Root, Mongolian Snakegourd Fruit, Magnolia Bark, Peppermint Herb and Baked Liquorice Root. The preparation method contains providing Heartleaf Houttuynia, Indigowood Root, Fineleaf Nepeta, Saposhnikovia Root, Mulberry Leaf, Scutellaria Root, Mongolian Snakegourd Fruit, Magnolia Bark, Peppermint Herb and Baked Liquorice Root; and soaking all the herbs described above in water and boiling the water to prepare a herbal liquid, the volume of which is about one-third of an initial volume of the water.

5 Claims, 7 Drawing Sheets

(56) References Cited

OTHER PUBLICATIONS

Taiwan Herbal Pharmacopeia 3rd Edition English Version, Ministry of Health and Welfare, Taiwan(R.O.C.), Dec. 2019.
Taiwan Application Serial No. 109135954, Office Action dated Jun. 15, 2021 and its translation.
Taiwan Application Serial No. 109135954, Claims in Response filed Aug. 12, 2021 to Office action dated Jun. 15, 2021 and its translation.
Taiwan Application Serial No. 109135954, Notice of Allowance dated Aug. 18, 2021 and its translation.

* cited by examiner

COMPOSITION OF PLANT INGREDIENTS, HERBAL COMPOSITION AND PREPARATION METHOD OF THE HERBAL COMPOSITION

CROSS-REFERENCE TO RELATED APPLICATION

This non-provisional application claims priority under 35 U.S.C. § 119(e) on U.S. provisional Patent Application No. 63/025,224 filed on May 15, 2020 and U.S. provisional Patent Application No. 63/026,733 filed on May 19, 2020, the entire contents of which are hereby incorporated by reference.

BACKGROUND OF THE INVENTION

1. Field of the Invention

The present disclosure relates to a composition of plant ingredients, a herbal composition and a preparation method of the herbal composition, and in particular to a composition that can inhibit coronavirus.

2. Description of the Related Art

Coronavirus Disease 2019 (COVID-19) is an acute pneumonia caused by Severe Acute Respiratory Syndrome Coronavirus 2 (hereinafter referred to as SARS-CoV-2), which has currently caused large-scale infections worldwide. The main transmission route of SARS-CoV-2 is droplet infection or contact infection. The incubation period from SARS-CoV-2 infection to onset is 1 to 14 days. Common symptoms of patients with COVID-19 include fever, dry cough, fatigue, shortness of breath, muscle pain, headache, sore throat, diarrhea, and loss of smell or taste, etc.

BRIEF SUMMARY OF THE INVENTION

However, so far no drugs have been developed that can effectively response to COVID-19. The main administration method for COVID-19 is to use supportive therapy. Although there are currently several old drugs used to test their therapeutic effects against COVID-19, for example, Remdesivir or hydroxychloroquine, the efficacy of these old drugs against COVID-19 has not been fully confirmed yet.

An object of the present invention is to provide a composition of plant ingredients in view of the above problems. The composition of plant ingredients comprises Heartleaf Houttuynia, Indigowood Root, Fineleaf Nepeta, Saposhnikovia Root, Mulberry Leaf, Scutellaria Root, Mongolian Snakegourd Fruit, Magnolia Bark, Peppermint Herb and Baked Liquorice Root.

The composition of plant ingredients described above comprises Heartleaf Houttuynia, Indigowood Root, Fineleaf Nepeta, Saposhnikovia Root, Mulberry Leaf, Scutellaria Root, Mongolian Snakegourd Fruit, Magnolia Bark, Peppermint Herb and Baked Liquorice Root, wherein the parts by weight of each plant ingredient is 1 to 20.

The composition of plant ingredients described above comprises 5 parts by weight of Heartleaf Houttuynia, 5 parts by weight of Indigowood Root, 3 parts by weight of Fineleaf Nepeta, 2 parts by weight of Saposhnikovia Root, 3 parts by weight of Mulberry Leaf, 5 parts by weight of Scutellaria Root, 5 parts by weight of Mongolian Snakegourd Fruit, 3 parts by weight of Magnolia Bark, 3 parts by weight of Peppermint Herb and 2 parts by weight of Baked Liquorice Root.

To achieve the above and other objects, the present invention provides a herbal composition, which comprises Heartleaf Houttuynia, Indigowood Root, Fineleaf Nepeta, Saposhnikovia Root, Mulberry Leaf, Scutellaria Root, Mongolian Snakegourd Fruit, Magnolia Bark, Peppermint Herb and Baked Liquorice Root.

The herbal composition described above comprises Heartleaf Houttuynia, Indigowood Root, Fineleaf Nepeta, Saposhnikovia Root, Mulberry Leaf, Scutellaria Root, Mongolian Snakegourd Fruit, Magnolia Bark, Peppermint Herb and Baked Liquorice Root, wherein the parts by weight of each herbal is 1 to 20.

To achieve the above and other objects, the present invention provides a herbal composition for inhibiting coronavirus. The herbal composition comprises Heartleaf Houttuynia, Indigowood Root, Fineleaf Nepeta, Saposhnikovia Root, Mulberry Leaf, Scutellaria Root, Mongolian Snakegourd Fruit, Magnolia Bark, Peppermint Herb and Baked Liquorice Root, wherein the parts by weight of each herbal is 1 to 20.

The herbal composition described above comprises 5 parts by weight of Heartleaf Houttuynia, 5 parts by weight of Indigowood Root, 3 parts by weight of Fineleaf Nepeta, 2 parts by weight of Saposhnikovia Root, 3 parts by weight of Mulberry Leaf, 5 parts by weight of Scutellaria Root, 5 parts by weight of Mongolian Snakegourd Fruit, 3 parts by weight of Magnolia Bark, 3 parts by weight of Peppermint Herb and 2 parts by weight of Baked Liquorice Root.

To achieve the above and other objects, the present invention provides a herbal composition for inhibiting cytokine storm. The herbal composition comprises Heartleaf Houttuynia, Indigowood Root, Fineleaf Nepeta, Saposhnikovia Root, Mulberry Leaf, Scutellaria Root, Mongolian Snakegourd Fruit, Magnolia Bark, Peppermint Herb and Baked Liquorice Root, wherein the parts by weight of each herbal is 1 to 20.

The herbal composition described above comprises 5 parts by weight of Heartleaf Houttuynia, 5 parts by weight of Indigowood Root, 3 parts by weight of Fineleaf Nepeta, 2 parts by weight of Saposhnikovia Root, 3 parts by weight of Mulberry Leaf, 5 parts by weight of Scutellaria Root, 5 parts by weight of Mongolian Snakegourd Fruit, 3 parts by weight of Magnolia Bark, 3 parts by weight of Peppermint Herb and 2 parts by weight of Baked Liquorice Root.

To achieve the above and other objects, the present invention provides a preparation method of a herbal composition for inhibiting coronavirus. The preparation method comprises (a) providing 5 parts by weight of Heartleaf Houttuynia, 5 parts by weight of Indigowood Root, 3 parts by weight of Fineleaf Nepeta, 2 parts by weight of Saposhnikovia Root, 3 parts by weight of Mulberry Leaf, 5 parts by weight of Scutellaria Root, 5 parts by weight of Mongolian Snakegourd Fruit, 3 parts by weight of Magnolia Bark, 3 parts by weight of Peppermint Herb and 2 parts by weight of Baked Liquorice Root; and (b) soaking all herbs provided in step (a) in water and boiling the water to prepare a herbal liquid, the volume of the herbal liquid is about one-third of an initial volume of the water.

The composition of plant ingredients, the herbal composition and the preparation method of the herbal composition described above can be used to inhibit coronavirus and, in particular, SARS-CoV-2 that causes COVID-19.

DETAILED DESCRIPTION OF THE INVENTION

To facilitate understanding of the object, characteristics and effects of this present disclosure, embodiments together with the attached drawings for the detailed description of the present disclosure are provided.

Preparation of the Herbal Composition NRICM101:

First, 18.75 g of Heartleaf Houttuynia, 18.75 g of Indigowood Root, 11.25 g of Fineleaf Nepeta, 7.5 g of Saposhnikovia Root, 11.25 g of Mulberry Leaf, 18.75 g of Scutellaria Root, 18.75 g of Mongolian Snakegourd Fruit, 11.25 g of Magnolia Bark, 11.25 g of Peppermint Herb and 7.5 g of Baked Liquorice Root (i.e., 5 parts by weight of Heartleaf Houttuynia, 5 parts by weight of Indigowood Root, 3 parts by weight of Fineleaf Nepeta, 2 parts by weight of Saposhnikovia Root, 3 parts by weight of Mulberry Leaf, 5 parts by weight of Scutellaria Root, 5 parts by weight of Mongolian Snakegourd Fruit, 3 parts by weight of Magnolia Bark, 3 parts by weight of Peppermint Herb and 2 parts by weight of Baked Liquorice Root) are provided. Next, the ten kinds of herbs described above are soaked in 1 liter of water and boiled to form a herbal liquid, the volume of the herbal liquid is about 300 ml. The herbal composition prepared through the above steps is named NRICM101. In the preparation process of NRICM101, the amount of water for soaking the herbs can be increased or decreased according to demand, as long as the volume of the herbal liquid is about one-third of the initial amount of water in which the herbs are soaked.

Observation Study of the Herbal Composition NRICM101:

First, 33 patients with confirmed COVID-19 were observed. The study method is as follows. 21 patients of the non-NRICM101 group were treated according to their symptoms only during the hospitalization period, which means the non-NRICM101 group was given symptomatic care, while 12 patients of the NRICM101 group were received the herbal composition NRICM101 during hospitalization. Both the non-NRICM101 group and the NRICM101 group were sampled their respiratory tract. Only those whose respiratory pathogen test results were negative for three consecutive samplings (with a sampling interval of longer than 24 hours) could be discharged.

The administration of NRICM101 is as follow. Three doses of NRICM101 were given to the patient every day until the patient was discharged, each dose of NRICM101 was 100 ml and administered orally 30 minutes after the meal. Patient discharge criteria is as follow: the patients' respiratory tracts were sampled, and only those whose respiratory pathogen test results were negative for three consecutive samplings (with a sampling interval of longer than 24 hours) could be discharged.

Figure 1:
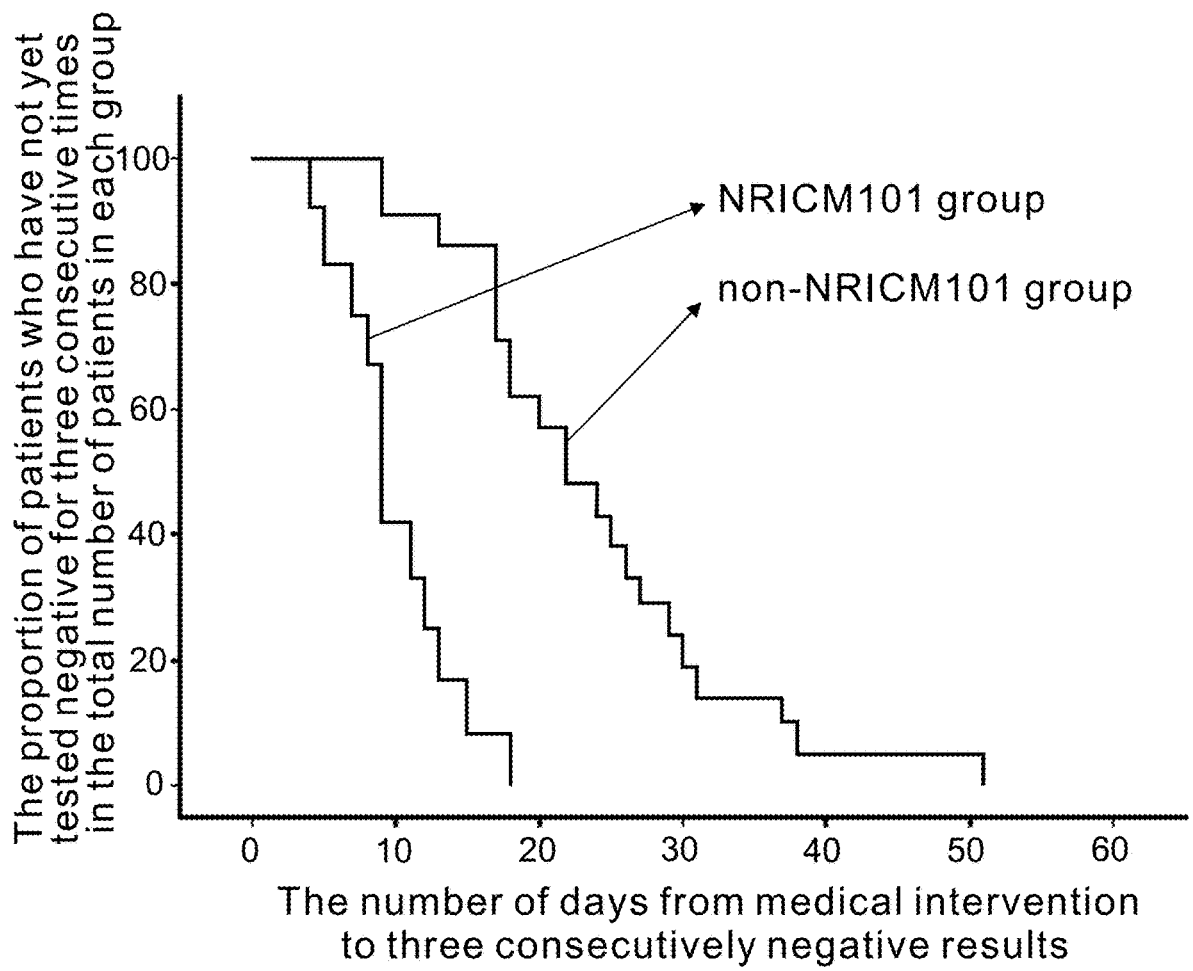
FIG. 1 shows the result of the observation study of the NRICM101 group and the non-NRICM101 group.

The result of observation study is shown in FIG. 1, which is a Kaplan-Meier survival curve chart showing the distributions of numbers of days when three consecutive negative results were obtained in the non-NRICM101 group and the NRICM101 group. In FIG. 1, the x-axis represents the number of days from the time point of medical intervention to the time point of obtaining three consecutively negative results, and the y-axis represents the proportion of patients who have not yet tested negative for three consecutive times in the total number of patients in each group. Regarding the number of days from the time point of medical intervention to the time point of obtaining three negative results, the median number of days in the non-NRICM101 group was 22 days, and the median number of days in the NRICM101 group was 9 days, it indicates that the number of days of three negative results in the non-NRICM101 group and NRICM101 group had reached statistically significant difference ($P<0.001$). The above results can confirm that NRICM101 has inhibitory effect on SARS-CoV-2.

Binding reactivity test of the herbal composition NRICM101 to the spike RBD protein of SARS-CoV-2:

In this example, the surface plasma resonance (SPR) method is used to determine the binding of NRICM101 to the receptor-binding domain (RBD) of the spike protein of SARS-CoV-2. The test procedure is as follow.

First, the receptor-binding domain (RBD) of the spike protein of SARS-CoV-2 (purchased from Sino Biological) was provided, and dissolved in the phosphate buffered saline (PBS) solution. The concentration of RBD was diluted to 25 μg/mL, and the diluted RBD was captured with NTA wafer (Nicoyalife). At the same time, NRICM101 was diluted with PBS solution to 1/5, 1/10, 1/20, 1/40, 1/80 and 1/160 dilution. Next, the SPR equipment OpenSPR (Nicoyalife) was used to analyze the binding ability of the above-mentioned NRICM101 with different dilution multiples to RBD. The flow rate of the analysis liquid was set at 20 μL/min. The measurement results obtained by SPR equipment OpenSPR were analyzed using TraceDrawer software (Nicoyalife).

Figure 2:
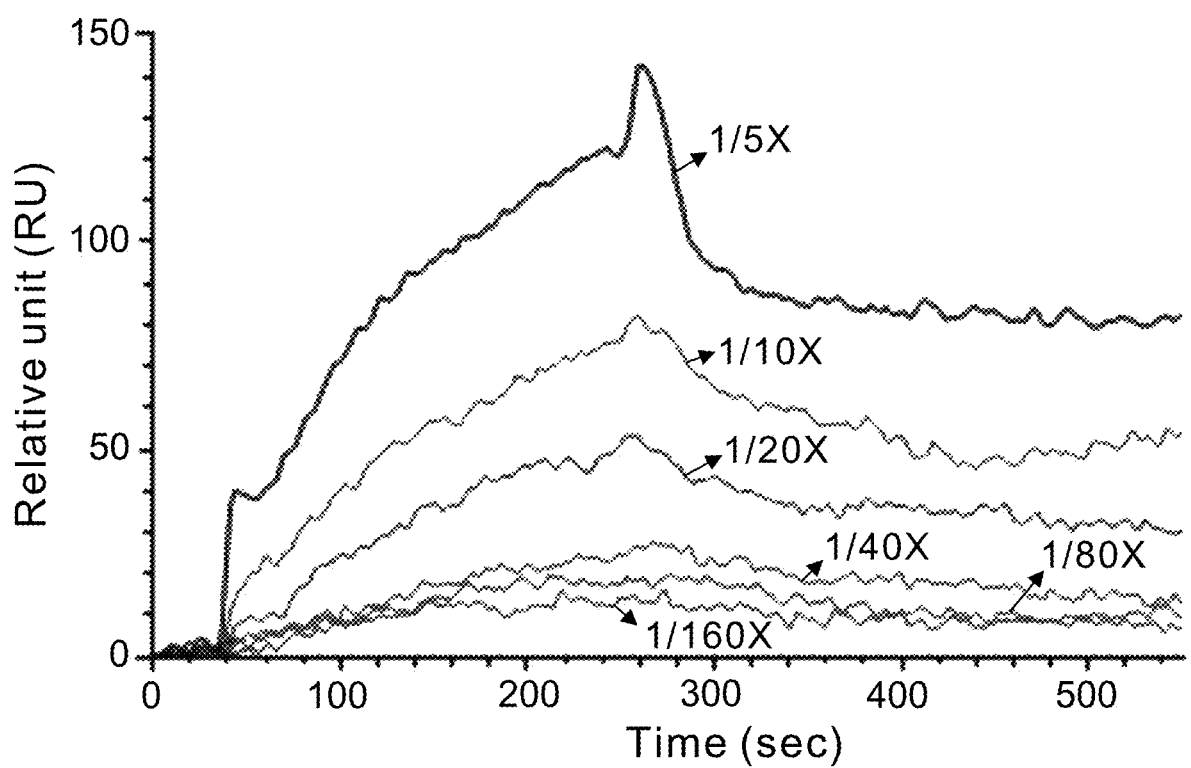
FIG. 2 shows the binding reactivity of the herbal composition NRICM101 according to an embodiment of the present invention to the spike RBD protein of SARS-CoV-2.

The above test results are shown in FIG. 2. NRICM101 with 1/5, 1/10 and 1/20 dilution has better binding effect on the receptor binding domain of the spike protein of SARS-CoV-2 and the binding effect of NRICM101 with the receptor-binding domain exhibits dose-dependent, which means the higher the concentration of NRICM101, the better the binding effect with the receptor-binding domain of the spike protein of SARS-CoV-2. According to current research, it is known that SARS-CoV-2 enters the cell by binding the receptor-binding domain of its spike protein to the transmembrane protein ACE2 on the cell surface during the process of infecting cells. Therefore, it is possible to prevent SARS-CoV-2 from entering human cells and infecting the human body by the binding of NRICM101 to the receptor-binding domain of the spike protein of SARS-CoV-2.

The inhibitory effect of NRICM101 on the interaction of the spike RBD protein of SARS-CoV-2 to the ACE2 receptor:

In this example, the enzyme-linked immunosorbent assay (ELISA) was used to determine the inhibitory effect of NRICM101 on the binding of SARS-CoV-2 spike protein to ACE2 receptors, that is, to measure the ability of NRICM101 and the spike protein of SARS-CoV-2 to compete for binding to the ACE2 receptor. The test procedure is as follow.

First, a 96-well micro-well plate was provided. Each well of the micro-well plate was coated with 0.2 µg of the receptor-binding domain of the spike protein of SARS-CoV-2 (purchased from Sino Biological). The non-specific binding sites of the spike protein of SARS-CoV-2 in the micro-well plate were blocked with 1% bovine serum albumin (BSA), and then the 1% BSA in the micro-well plate was cleaned with PBST solution (composed of PBS solution and Tween-20). Afterwards, the following dilutions of NRICM101 in PBS solution were prepared: 1/5, 1/10, 1/20, 1/40, 1/80, 1/160, 1/320, 1/640, 1/1280, 1/2560, and 1/5120, which were then added into each well so that the above NRICM101 samples reacted with the receptor-binding domain of the spike protein of SARS-CoV-2. The micro-well plate in which the NRICM101 samples at the above dilutions was added was placed in the incubator at 25° C. for 1 hour and waited for NRICM101 to react with the receptor-binding domain. After that, rabbit anti-His tag antibody-horseradish peroxidase (HRP) complex (purchased from Immunology consultants laboratory) was used to detect the reaction result of NRICM101 and the receptor-binding domain. Finally, 3,3',5,5'-tetramethylbenzidine (purchased from SeraCare) was added to each well of the micro-well plate for color development, and the reaction between NRICM101 and the receptor-binding domain in the micro-well plate was terminated with 1N HCl. After the reaction between NRICM101 and the receptor-binding domain in the micro-well plate was terminated, the full-spectrum absorption light interpreter SPECTROstar Nano (purchased from BMG LABTECH) was used to read the reaction results in the micro-well plate at the wavelength of $OD_{450}$ nm. The relative inhibition rate of the NRICM101 sample with different dilution against the binding of SARS-CoV-2 spike protein to ACE2 receptor was analyzed. The inhibitory effect of NRICM101 on 50% SARS-CoV-2 spike protein (i.e. $IC_{50}$) was calculated by software Prism.

Figure 3:
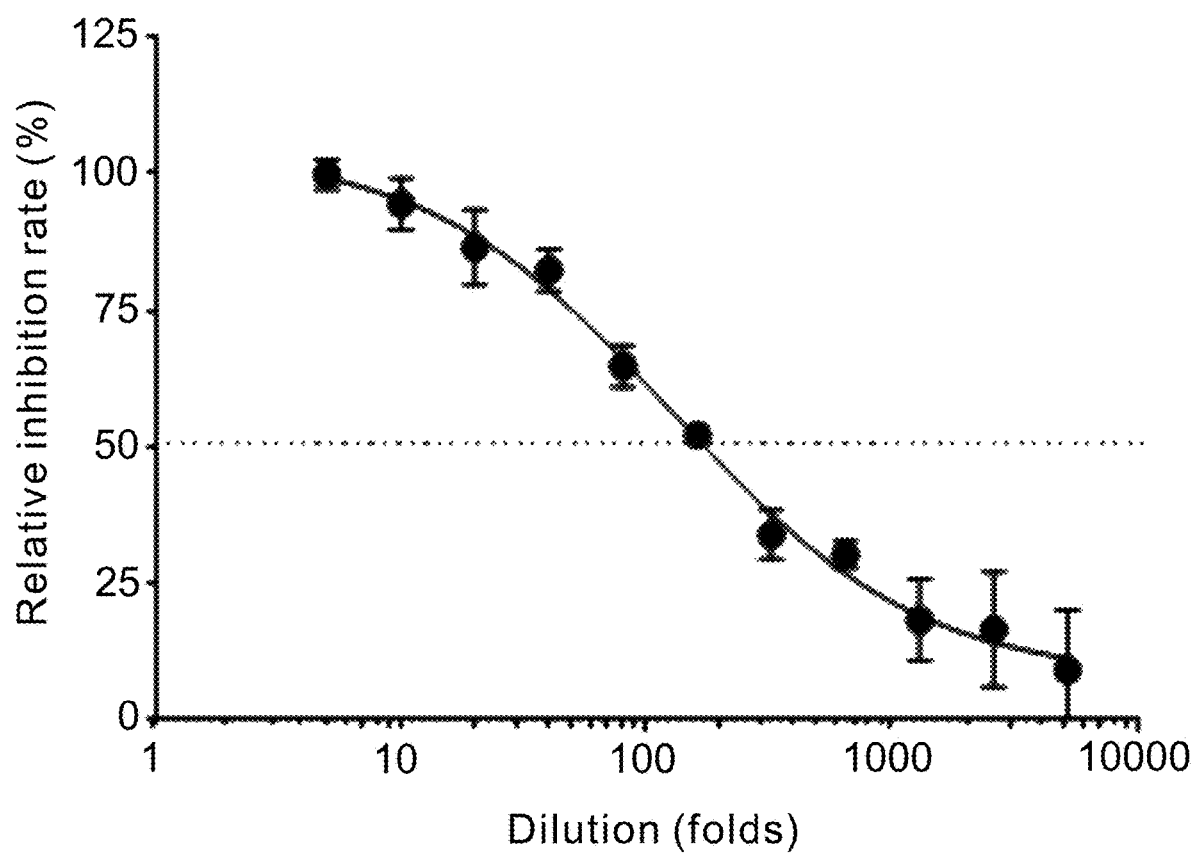
FIG. 3 shows that the interaction of the spike RBD protein of SARS-CoV-2 to the ACE2 receptor was inhibited by serially diluted NRICM101.

The above test results are shown in FIG. 3. NRICM101 has a good inhibitory effect on SARS-CoV-2 spike protein binding to ACE2 receptor, and the inhibitory effect is in a dose-dependent relationship. NRICM101 can inhibit 50% of SARS-CoV-2 spike protein when diluted by 128 folds (i.e. $IC_{50}$).

Inhibitory Effect of NRICM101 on 3CL Protease of SARS-CoV-2:

In this example, the inhibitory effect of NRICM101 on the 3CL protease of SARS-CoV-2 was determined through 3CL protease inhibition analysis. The test procedure is as follow.

First, a 384-well micro-well plate was provided. The following dilutions of NRICM101 in PBS solution were prepared: 1/5, 1/10, 1/20, 1/40, 1/80, 1/160, 1/320, 1/640, and 1/1280, which were then added into each well so that the NRICM101 samples with the above dilutions existed in the wells of the micro-well plate. 50 ng of recombinant SARS-CoV-2 3CL protease (purchased from Pharmtekx) and reaction solution (purchased from Sigma-Aldrich, containing 25 mM Tris, 100 mM NaCl, 1 mM EDTA and 1 mM DTT with a pH of 7.3) were added into each of the above NRICM101 samples with different dilution and incubated together for 30 minutes. The total volume of the 3CL protease, each NRICM101 sample and the reaction solution was 20 µl. The reactants composed of the NRICM101 samples with different dilutions, the 3CL protease and the reaction solution were used as the experimental group, while the reactant composed of the 3CL protease and the reaction solution only was provided in the micro-well plate as the control group. The micro-well plate was placed on ice. Afterwards, 0.25 µs of protease fluorescent matrix peptide Dabcyl-KT-SAVLQSGFRKME-Edans (purchased from Kelowna International Scientific) (at a final concentration of 6 µM) was added into each experimental group and control group in the micro-well plate to detect the activity of 3CL protease. One end of the protease fluorescent matrix peptide is Edans which emits fluorescence, and the other end is Dabcyl which absorbs fluorescence. When the protease fluorescent matrix peptide is cleaved by 3CL protease, the two ends of the protease fluorescent matrix peptide will be far away from each other and increase the amount of fluorescence. If the activity of 3CL protease was inhibited and the protease fluorescent matrix peptide cannot be cleaved off, the rate of increase in fluorescence will slow down. Based on the above principle, the above micro-well plate with the addition of protease fluorescent matrix peptide for reaction was put into the micro-well plate analyzer CLARIOstar (purchased from BMG LABTECH) to determine the effect of 3CL protease inhibition. The measurement conditions of the micro-well plate analyzer was set at 37° C., using excitation light of 355 nm, and monitoring the amount of fluorescence with a wavelength of 538 nm for one hour. Through the above test process, the inhibitory effect of NRICM101 on 3CL protease of SARS-CoV-2 was determined. The inhibitory effect of NRICM101 on 3CL protease of 50% SARS-CoV-2 (i.e. $IC_{50}$) was calculated by software Prism.

The calculation formula for the inhibitory effect of NRICM101 on 3CL protease of SARS-CoV-2 is as follow: Inhibition rate $(\%)=1-[(S-S_0)/(C-C_0)]\times 100$. C is the amount of fluorescence in the control group after adding 3CL protease, the reaction solution and fluorescent matrix peptide to the micro-well plate and reacting for 1 hour; $C_0$ is the amount of fluorescence in the control group where 3CL protease and fluorescent matrix peptide are at the starting point of the reaction; S is the amount of fluorescence in the experimental group after adding 3CL protease, NRICM101 with various dilutions, the reaction solution and fluorescent matrix peptide to the micro-well plate and reacting for 1 hour; and $S_0$ is the amount of fluorescence in the experimental group where 3CL protease and fluorescent matrix peptide are at the starting point of the reaction.

Figure 4:
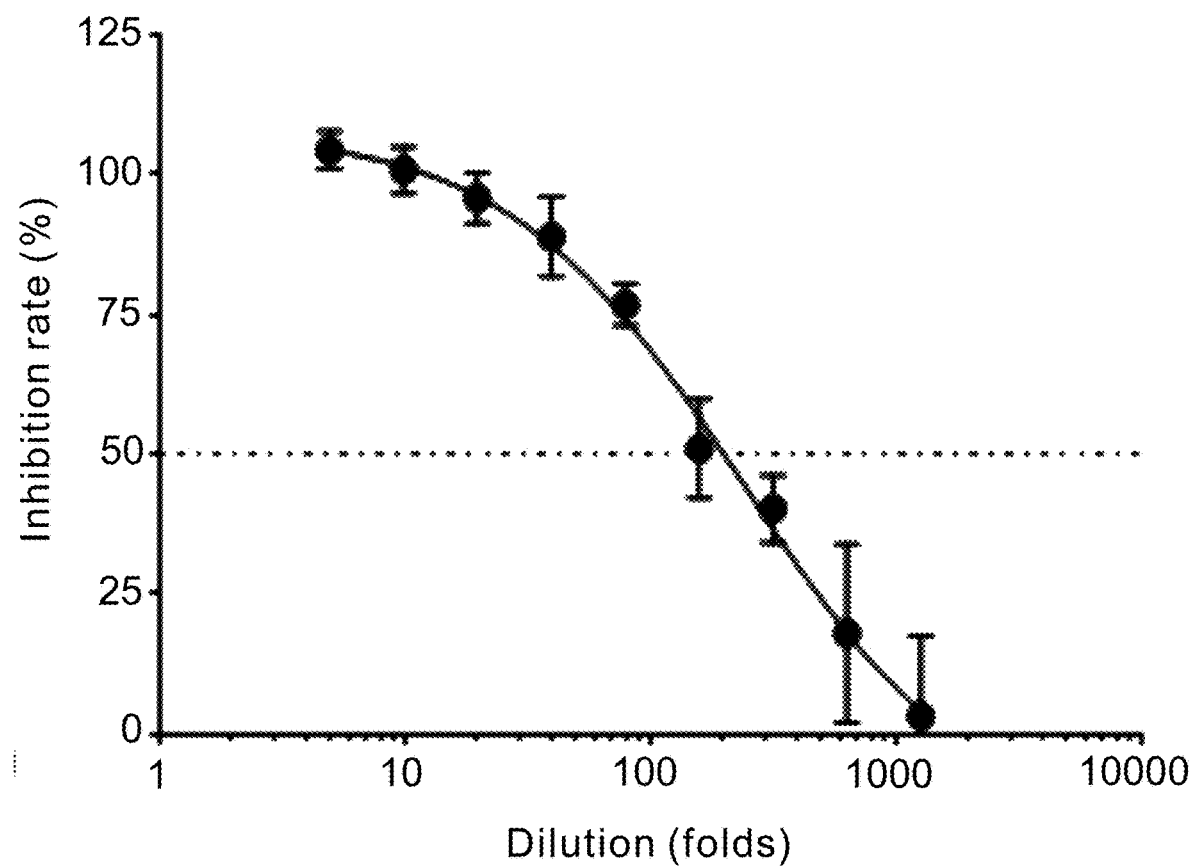
FIG. 4 shows that NRICM101 inhibited SARS-CoV-2 3CL protease activity.

The above test results are shown in FIG. 4. NRICM101 has a good inhibitory effect on 3CL protease of SARS-CoV-2, and the inhibitory effect is in a dose-dependent relationship. NRICM101 can inhibit 3CL protease of 50% SARS-CoV-2 (i.e. $IC_{50}$) when diluted by 244 folds. According to current research, it is known that 3CL protease of SARS-CoV-2 is a key protein in the intracellular replication process of SARS-CoV-2, and is mainly used to hydrolyze the SARS-CoV-2 polyproteins pp1a and pp1ab for producing the core protein required for SARS-CoV-2 replication. Therefore, the 3CL protease activity of SARS-CoV-2 can be inhibited through NRICM101, thereby preventing SARS-CoV-2 from replicating in cells.

The Inhibitory Effect of NRICM101 on SARS-CoV-2 Activity:

In this example, the immunofluorescent assay and virus plaque reduction neutralization test were used to determine the inhibitory effect of NRICM101 on SARS-CoV-2-infected cells. The test procedure is as follows.

Immunofluorescent Assay:

First, Vero E6 cells (obtained from the Biological Resources Conservation and Research Center) and SARS-CoV-2 (obtained from the Taiwan Disease Control Center) were prepared. Next, Vero E6 cells and SARS-CoV-2 were administered respectively with NRICM101 at 40, 80, 160, 320, and 640-fold dilutions at 37° C. for 1 hour. Afterwards, a 24-well cell culture plate was provided, and the SARS-CoV-2 sample administered with NRICM101 of 40-fold dilution and the corresponding Vero E6 cells (at a concentration of $5 \times 10^4$ cells per well) were added into one of the wells, other SARS-CoV-2 samples administered with NRICM101 of other dilution fold and the corresponding Vero E6 cells were added into other wells of the cell culture plate respectively in the same manner, thereby serving as five experimental groups. Vero E6 cells and SARS-CoV-2 that have not been administered with NRICM101 were added into another well of the cell culture plate as the control group. The cell culture plate having the experimental groups and the control group was placed at 37° C. for two days so that Vero E6 cells were infected by SARS-CoV-2 (at a virus concentration of 0.01 MOI).

Two days later, the Vero E6 cells in the five experimental groups and the control group were taken out, fixed with 10% formalin, and made transparent with 0.5% Triton X-100 dissolved in PBS solution. Afterwards, the transparent Vero E6 cells were dyed with human anti-SARS-CoV-2 monoclonal antibody (provided by Dr. Yang An-Suei, Genomic Research Center, Academia Sinica, Taiwan) and fluorescent dye goat anti-human IgG-Alexa Fluor 488. The nuclei of Vero E6 cells were stained with DAPI (D1306, purchased from Invitrogen). The results of Vero E6 cell staining were observed and photographed with an immunofluorescence microscope. The obtained cell fluorescence image was quantitatively analyzed by a multi-level fluorescence image capture and analysis system (ImageXpress Micro XLS Widefield High-Content Analysis System) (purchased from Molecular Devices).

At the same time, for the toxicity study of NRICM101 on Vero E6 cells, a cell viability test was performed. NRICM101 was diluted with PBS solution to 1/10, 1/20, 1/40, 1/80, 1/160, 1/320, 1/640, and 1/1280 dilutions. The Vero E6 cells were administered with NRICM101 at the above dilutions for one day at 37° C., and then the cell viability of Vero E6 cells administered with NRICM101 at the above dilutions was calculated by Cell Counting Kit-8. The concentration of NRICM101 inhibiting 50% of Vero E6 cells from not being infected (i.e., $IC_{50}$) and 50% Vero E6 cytotoxic concentration (i.e., $CC_{50}$) are calculated by software Prism.

Figure 5:
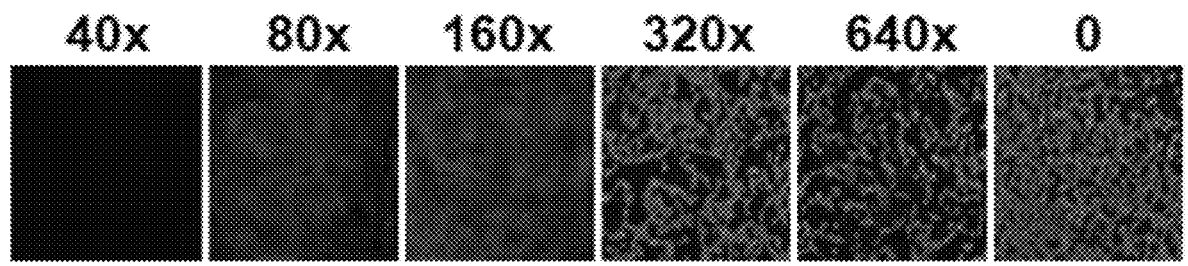
FIG. 5 shows the anti-SARS-CoV-2 data of the immunofluorescent assay.

The above immunofluorescent assay results are shown in FIG. 5. NRICM101 can inhibit SARS-CoV-2 from infecting Vero E6 cells, especially NRICM101 with 40 to 160-fold dilutions exhibited excellent effects on inhibiting SARS-CoV-2 from infecting Vero E6 cells.

Figure 6:
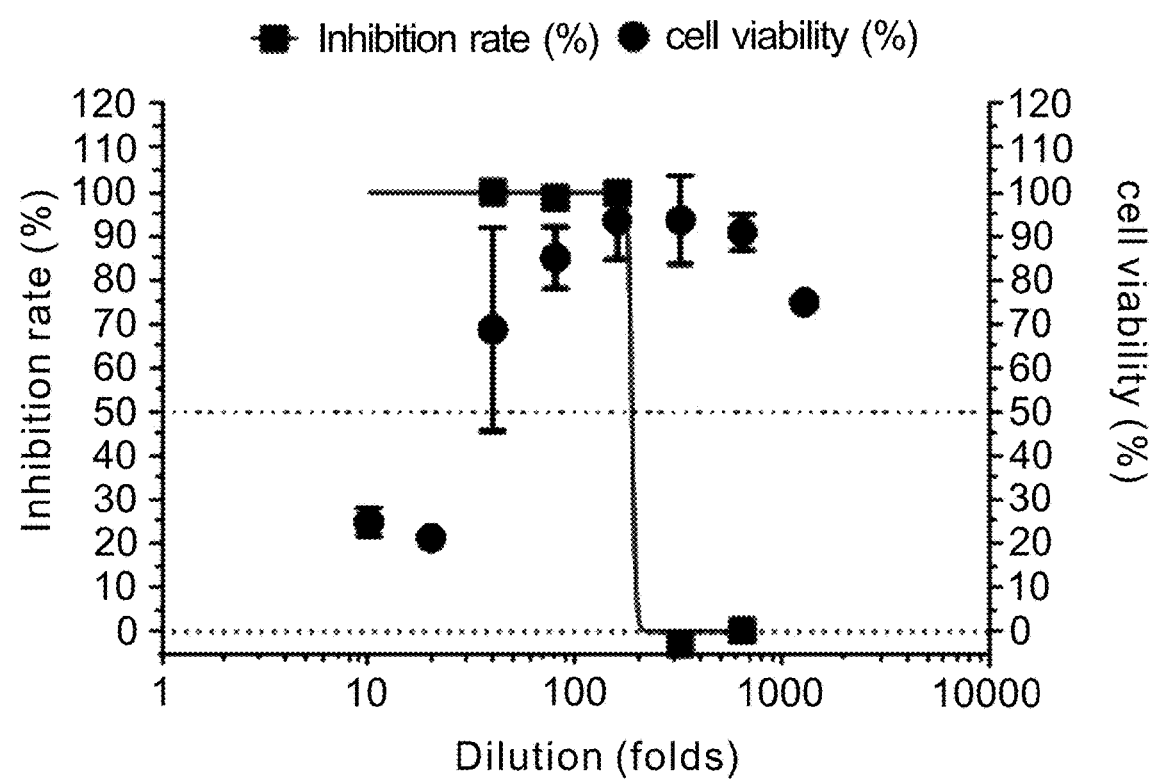
FIG. 6 shows the data of CCK-8 cell viability and viral infection in the immunofluorescent assay.

Referring again to FIG. 6, in which the five squares represent the inhibition rate data of the five experimental groups in FIG. 5, and the eight dots represent the data of the eight experimental groups in the cell viability test. NRICM101 at 187-fold dilution can prevent 50% of the Vero E6 cells from being infected (i.e. $IC_{50}$). NRICM101 at 30-fold dilution cause 50% of the cells to produce toxicity (i.e. $CC_{50}$).

SARS-CoV-2 Virus Plaque Reduction Neutralization Test:

First, Vero E6 cells (obtained from the Biological Resources Conservation and Research Center) and SARS-CoV-2 (obtained from the Taiwan Disease Control Center) were prepared. Next, Vero E6 cells and SARS-CoV-2 were administered with NRICM101 of 20, 40, 80, 160, and 320-fold dilutions at 37° C. for 1 hour. Afterwards, a 24-well cell culture plate was provided, and the Vero E6 cells administered with NRICM101 of 40-fold dilution and the SARS-CoV-2 administered with NRICM101 of 40-fold dilution were added into one of the wells (with a Vero E6 cell concentration of $5 \times 10^4$ cells per well and a SARS-CoV-2 virus concentration of 1 MOI), other SARS-CoV-2 samples and Vero E6 cells administered with NRICM101 of other dilution fold were processed in the same manner, thereby serving as five samples of the experimental group, while SARS-CoV-2 and Vero E6 cells that had not been administered with NRICM101 were processed in the same manner to serve as the sample of the control group. All the samples of the five experimental groups and the control group were placed at 37° C. for 1 hour to allow the virus entering the cells. After the samples of the experimental groups and the control group were left to stand for 1 hour, the virus fluid in the samples was removed, and then the cells in the samples of the experimental groups and the control group were covered with MEM medium containing 1% methylcellulose and kept at 37° C. for four days. At this time, the virus proliferated in the cells and caused the cells to rupture and die. Four days later, the cells in the samples of the experimental groups and the control group were fixed with 10% formalin and stained with crystal violet. The living cells appeared blue-purple, and the dead cells will not be dyed. Therefore, by observing the color distribution of the samples in the experimental groups and the control group, the spread of SARS-CoV-2 virus in each sample could be known.

Figure 7:
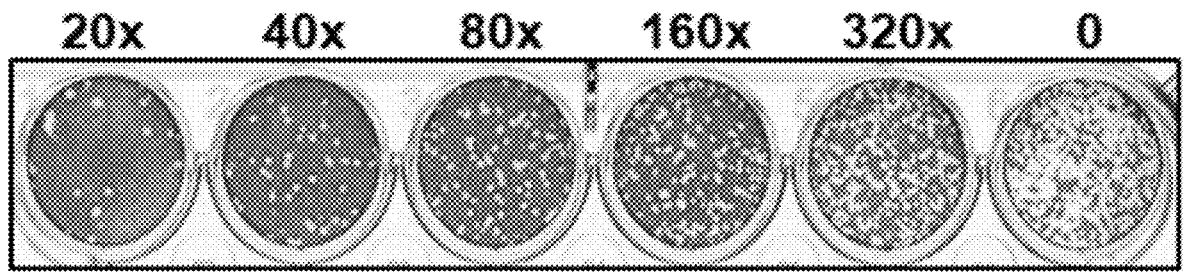
FIG. 7 shows the anti-SARS-CoV-2 data of plaque reduction neutralization test.

The results of the virus plaque test are shown in FIG. 7. The results of the virus plaque test show a dose-dependent relationship. NRICM101 can prevent the formation of SARS-CoV-2 plaques, that is, NRICM101 can inhibit the growth of SARS-CoV-2.

Both the above immunofluorescent assay results and virus plaque test results confirmed the inhibitory effect of NRICM101 on SARS-CoV-2 activity in cells.

Test of NRICM101 on Suppressing Cytokine Expression:

In this example, the effect of NRICM101 on suppressing cytokine expression was further determined. The test procedure is as follow.

First, $5 \times 10^5$ MH-S murine alveolar macrophages (CRL-2019 cells, purchased from ATCC) were cultured in a 12-well culture plate for 24 hours, and then NRICM101 was diluted with PBS solution to 1/5, 1/10, 1/20, 1/40, 1/80, 1/160, 1/320, 1/640, 1/1280, 1/2560, and 1/5120 dilutions. The murine alveolar macrophages were administered with NRICM101 of the above dilutions, and the murine alveolar macrophages administered with NRICM101 of the above dilutions were used as the samples of the experimental group. At the same time, the murine alveolar macrophages that were not administered with NRICM101 were prepared to serve as the sample of the control group. The samples of both the experimental group and the control group were added with lipopolysaccharide (LPS) (at a concentration of 1 μg/mL), and left to stand for 24 hours to induce inflammation in the cells, thereby causing intracellular expression of the cytokines TNF-α and IL-6. TNF-α and IL-6 are the cytokines that are initially expressed when the inflammation reaction occurs in the cells, and can be used as indicators of the expression of intracellular cytokines. The TNF-α and IL-6 yields in cells were measured with a commercial ELISA kit (purchased from R&D Systems). The concentration of NRICM101 inhibiting expression of 50% IL-6 and 50% TNF-α (i.e., $IC_{50}$) was calculated by software Prism.

Figure 8:
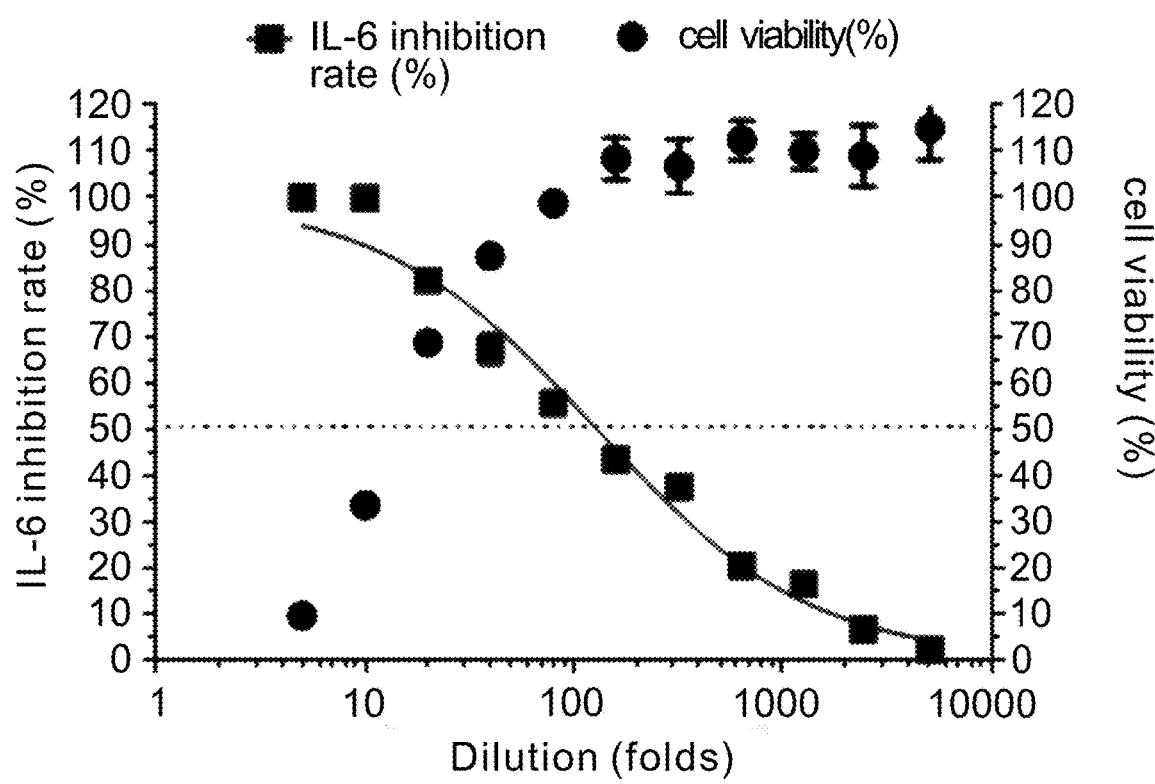
FIG. 8 shows that NRICM101 inhibited LPS-induced expression of IL-6 in murine alveolar macrophages.
Figure 9:
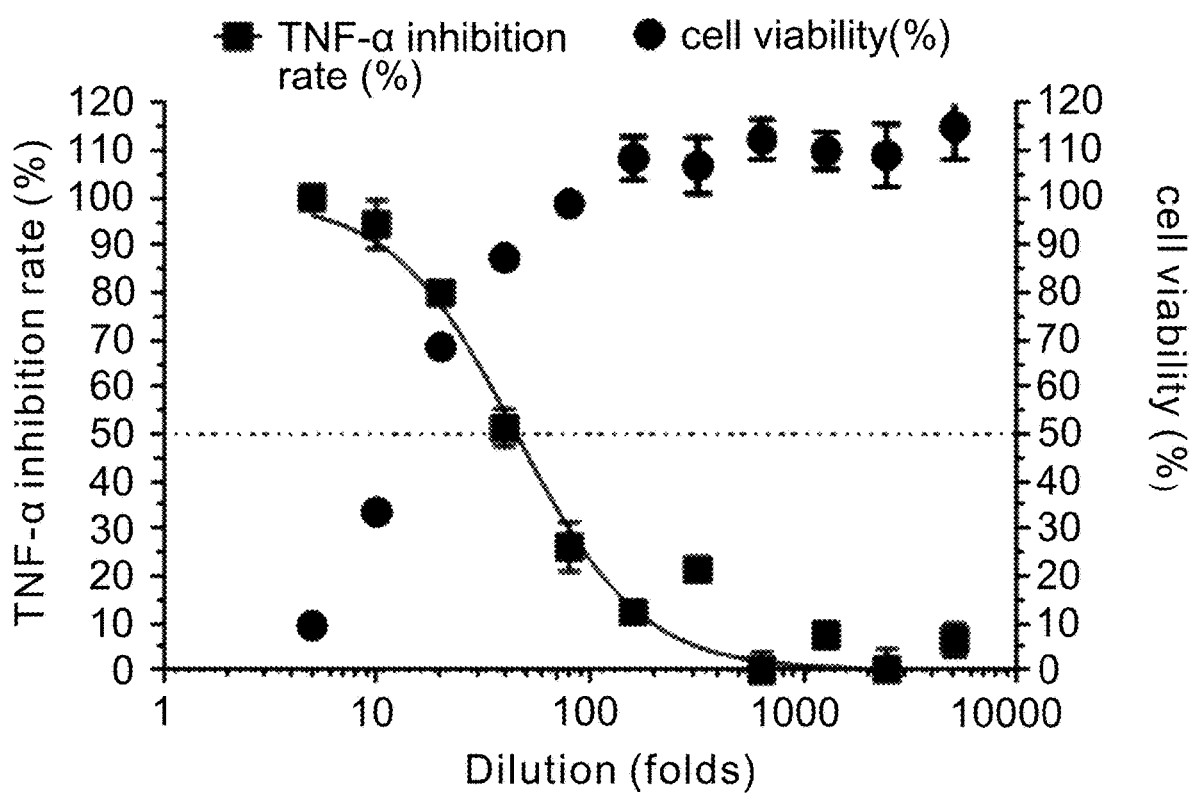
FIG. 9 shows that NRICM101 inhibited LPS-induced expression of TNF-α in murine alveolar macrophages.

The above test results are shown in FIGS. 8 and 9. NRICM101 has a good inhibitory effect on TNF-α and IL-6 expressions in cells, in which NRICM101 can inhibit 50% TNF-α expression (i.e., $IC_{50}$) when diluted by 128 folds and 50% IL-6 expression (i.e., $IC_{50}$) when diluted by 45 folds. According to current research, it is known that when a patient is infected with SARS-CoV-2, a cytokine storm will occur, which will cause a violent immune response in the patient's body, and the excessive immune response can cause organ damage and even cause death. Therefore, the above test results confirm that NRICM101 can also help suppress the cytokine storm in the patient's body and prevent the patient's condition from getting worse after being infected with SARS-CoV-2.

As mentioned above, NRICM101 can bind to the spike protein of SARS-CoV-2, while inhibiting the spike protein of SARS-CoV-2 from binding to the ACE2 receptor, thereby preventing SARS-CoV-2 from entering the cell. Furthermore, NRICM101 can also inhibit the 3CL protease activity of SARS-CoV-2, thereby preventing SARS-CoV-2 from replicating in cells. On the other hand, NRICM101 also has an inhibitory effect on the activity of SARS-CoV-2 in cells. In addition, NRICM101 can also help suppress the cytokine storm in the patient's body and prevent the patient's condition from getting worse after being infected with SARS-CoV-2. Therefore, NRICM101 can effectively inhibit SARS-CoV-2 and be used to fight against COVID-19.

The above examples have exemplified the efficacy of the herbal composition NRICM101 in the treatment of SARS-CoV-2 that causes COVID-19. However, in other embodiments, the composition ratio of each component different from that of NRICM101 as well as the preparation method of NRICM101 described above can be used to prepare other plant ingredient compositions composed of Heartleaf Houttuynia, Indigowood Root, Fineleaf Nepeta, Saposhnikovia Root, Mulberry Leaf, Scutellaria Root, Mongolian Snakegourd Fruit, Magnolia Bark, Peppermint Herb and Baked Liquorice Root for application to preparation of drugs that inhibit various types of coronaviruses. In particular, Heartleaf Houttuynia, Indigowood Root, Fineleaf Nepeta, Saposhnikovia Root, Mulberry Leaf, Scutellaria Root, Mongolian Snakegourd Fruit, Magnolia Bark, Peppermint Herb and Baked Liquorice Root, each of which is 1 to 20 parts by weight, can be prepared into various herbal compositions and applied to treatment of diseases caused by coronaviruses.

While the present disclosure has been described by means of specific embodiments, numerous modifications and variations could be made thereto by those skilled in the art without departing from the scope and spirit of the present disclosure set forth in the claims.

What is claimed is:

1. A composition of plant ingredients, comprising 5 parts by weight of an aqueous extract of Heartleaf Houttuynia, 5 parts by weight of an aqueous extract of Indigowood Root, 3 parts by weight of an aqueous extract of Fineleaf Nepeta, 2 parts by weight of an aqueous extract of Saposhnikovia Root, 3 parts by weight of an aqueous extract of Mulberry Leaf, 5 parts by weight of an aqueous extract of Scutellaria Root, 5 parts by weight of an aqueous extract of Mongolian Snakegourd Fruit, 3 parts by weight of an aqueous extract of Magnolia Bark, 3 parts by weight of an aqueous extract of Peppermint Herb and 2 parts by weight of an aqueous extract of Baked Liquorice Root.

2. A herbal composition, comprising 5 parts by weight of an aqueous extract of Heartleaf Houttuynia, 5 parts by weight of an aqueous extract of Indigowood Root, 3 parts by weight of an aqueous extract of Fineleaf Nepeta, 2 parts by weight of an aqueous extract of Saposhnikovia Root, 3 parts by weight of an aqueous extract of Mulberry Leaf, 5 parts by weight of an aqueous extract of Scutellaria Root, 5 parts by weight of an aqueous extract of Mongolian Snakegourd Fruit, 3 parts by weight of an aqueous extract of Magnolia Bark, 3 parts by weight of an aqueous extract of Peppermint Herb and 2 parts by weight of an aqueous extract of Baked Liquorice Root.

3. A herbal composition for inhibiting coronavirus, comprising 5 parts by weight of an aqueous extract of Heartleaf Houttuynia, 5 parts by weight of an aqueous extract of Indigowood Root, 3 parts by weight of an aqueous extract of Fineleaf Nepeta, 2 parts by weight of an aqueous extract of Saposhnikovia Root, 3 parts by weight of an aqueous extract of Mulberry Leaf, 5 parts by weight of an aqueous extract of Scutellaria Root, 5 parts by weight of an aqueous extract of Mongolian Snakegourd Fruit, 3 parts by weight of an aqueous extract of Magnolia Bark, 3 parts by weight of an aqueous extract of Peppermint Herb and 2 parts by weight of an aqueous extract of Baked Liquorice Root.

4. A herbal composition for inhibiting cytokine storm, comprising 5 parts by weight of an aqueous extract of Heartleaf Houttuynia, 5 parts by weight of an aqueous extract of Indigowood Root, 3 parts by weight of an aqueous extract of Fineleaf Nepeta, 2 parts by weight of an aqueous extract of Saposhnikovia Root, 3 parts by weight of an aqueous extract of Mulberry Leaf, 5 parts by weight of an aqueous extract of Scutellaria Root, 5 parts by weight of an aqueous extract of Mongolian Snakegourd Fruit, 3 parts by weight of an aqueous extract of Magnolia Bark, 3 parts by weight of an aqueous extract of Peppermint Herb and 2 parts by weight of an aqueous extract of Baked Liquorice Root.

5. A preparation method of a herbal composition for inhibiting coronavirus, comprising:
   (a) providing 5 parts by weight of Heartleaf Houttuynia, 5 parts by weight of Indigowood Root, 3 parts by weight of Fineleaf Nepeta, 2 parts by weight of Saposhnikovia Root, 3 parts by weight of Mulberry Leaf, 5 parts by weight of Scutellaria Root, 5 parts by weight of Mongolian Snakegourd Fruit, 3 parts by weight of Magnolia Bark, 3 parts by weight of Peppermint Herb and 2 parts by weight of Baked Liquorice Root; and
   (b) soaking all the herbs provided in step (a) in 266 to 267 parts by weight of water and boiling the water to prepare a herbal liquid, the volume of the herbal liquid is about one-third of an initial volume of the water.

* * * * *